(12) United States Patent
Glock et al.

(10) Patent No.: US 6,555,499 B1
(45) Date of Patent: Apr. 29, 2003

(54) HERBICIDE AGENT

(75) Inventors: Jutta Glock, Mumpf (CH); Adrian Alberto Friedmann, Basel (CH); Derek Cornes, Allschwil (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/069,829

(22) PCT Filed: Sep. 5, 2000

(86) PCT No.: PCT/EP00/08659

§ 371 (c)(1),
(2), (4) Date: Feb. 26, 2002

(87) PCT Pub. No.: WO01/17352

PCT Pub. Date: Mar. 15, 2001

(30) Foreign Application Priority Data

Sep. 7, 1999 (CH) .............................. 1640/99

(51) Int. Cl.[7] .......................... A01N 43/40; A01N 43/58
(52) U.S. Cl. ....................... 504/130; 504/136
(58) Field of Search ................ 504/105, 130, 504/137

Primary Examiner—Alton Pryor
(74) Attorney, Agent, or Firm—Rose M. Allen

(57) ABSTRACT

Selectively herbicidal composition for the control of grasses and weeds in crops of useful plants, comprising a) a herbicidally effective amount of a compound of formula I

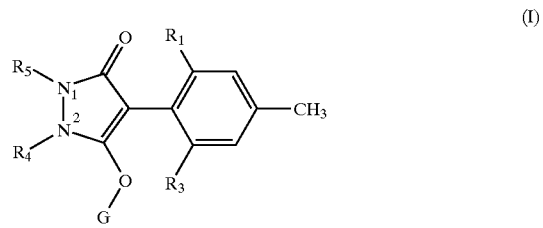

wherein the substituents are as defined in claim 1;

b) an amount, which is effective for antagonism of the herbicide, of a safener selected from cloquintocet, an alkal metali, alkaline earth metal, sulfonium or ammonium cation of cloquintocet, or cloquintocet-mexyl, mefenpyr, an alkali metal, alkaline earth metal, sulfonium or ammonium cation of mefenpyr, and mefenpyr-diethyl; and c) an additive comprising an oil of vegetable or animal origin, or a mineral oil, alkyl esters thereof or mixtures of those oils and oil derivatives.

3 Claims, No Drawings

HERBICIDE AGENT

This appl'n is a 371 of PCT/EP00/08659 filed Sep. 5, 2000.

A The present invention relates to new selectively herbicidal compositions for controlling grasses and weeds in crops of useful plants, especially in crops of maize and cereals, which compositions comprise a 3-hydroxy-4-(4-methylphenyl)-5-oxo-pyrazoline herbicide, a safener (counter-agent, antidote) and an oil additive and protect the useful plants but not the weeds against the phytotoxic action of the herbicide, and to the use of such compositions in controlling weeds in crops of useful plants.

When using herbicides, the cultivated plants may also suffer considerable damage, depending on, for example, the amount of herbicide used and the method of application, the cultivated plant, the nature of the soil and climatic conditions, for example hours of daylight, temperature and amounts of rainfall. In order to deal with that and similar problems, various substances have already been proposed as safeners, which are capable of antagonising the harmful effect of the herbicide on the cultivated plant, that is to say are capable of protecting the cultivated plant, without appreciably impairing the herbicidal action on the weeds to be acontrolled.

It has been found that the proposed safeners often act very specifically both with respect to the cultivated plants and with respect to the herbicide, and in some cases also in dependence on the method of application, that is to say, a particular safener is often suitable only for a particular cultivated plant and a specific class of herbicidal substance or a particular herbicide. For example, it has been found that although the safeners cloquintocet and cloquintocet-mexyl and mefenpyr and mefenpyr-diethyl, known from EP-A-0 191 736 (compound 1.316) and WO 91/07874 (Example 3) and from The Pesticide Manual, 11th Ed., British Crop Protection Council, Entry No. 154 and 462, are capable of protecting the cultivated plant from the phytotoxic action of particular 3-hydroxy-4-(4-methylphenyl)-5-oxo-pyrazoline derivatives, they do, however, reduce the herbicidal action on weeds in some cases.

U.S. Pat. No. 4,834,908 discloses that certain oil additive combinations can increase the herbicidal activity of compounds from the class of the cyclohexanediones, benzothiadiazinone dioxides, diphenyl ether herbicides and aryloxyphenoxy herbicides.

Although the 3-hydroxy-4-(4-methylphenyl)-5-oxo-pyrazoline derivatives are structurally completely different from the compounds disclosed in U.S. Pat. No. 4,834,908, the combination of such oil additives with the said 3-hydroxy-4-(4-methylphenyl)-5-oxo-pyrazoline derivatives likewise results in an increase in herbicidal activity but the cultivated plant is also damaged to a considerable extent. That herbicide/oil additive mixture is therefore not suitable for selectively controlling weeds in crops of useful plants.

It has now been found, surprisingly, that weeds can be selectively controlled very successfully using the particular 3-hydroxy-4-(4-methylphenyl)-5-oxo-pyrazoline herbicides without damaging the cultivated plant, by applying those compounds in combination with an additive comprising an oil of vegetable or animal origin or a mineral oil, alkyl esters thereof, or mixtures of those oils and oil derivatives, and with the safeners cloquintocet or mefenpyr.

The present invention accordingly relates to a selectively herbicidal composition that, in addition to comprising customary inert formulation adjuvants such as carriers, solvents and wetting agents, comprises as active ingredient a mixture of a) a herbicidally effective amount of a compound of formula I

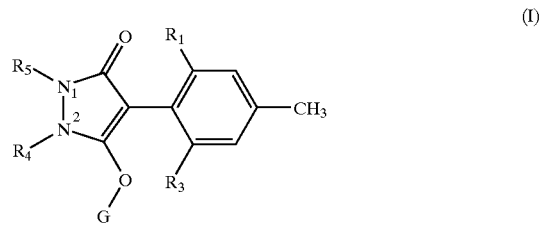

(I)

wherein $R_1$ and $R_3$ are, each independently of the other, halogen, nitro, cyano, $C_1$–$C_4$alkyl, $C_2$–$C_4$-alkenyl, $C_2$–$C_4$alkynyl, $C_1$–$C_4$haloalkyl, $C_2$–$C_6$haloalkenyl, $C_3$–$C_6$cycloalkyl, halo-substituted $C_3$–$C_6$cycloalkyl, $C_2$–$C_6$alkoxyalkyl, $C_2$–$C_6$alkylthioalkyl, hydroxy, mercapto, $C_1$–$C_6$alkoxy, $C_3$–$C_6$alkenyloxy, $C_3$–$C_6$alkynyloxy, carbonyl, carboxyl, $C_1$–$C_4$alkylcarbonyl, $C_1$–$C_4$hydroxyalkyl, $C_1$–$C_4$alkoxycarbonyl, $C_1$–$C_4$alkylthio, $C_1$–$C_4$alkylsulfinyl, $C_1$–$C_4$alkylsulfonyl, amino, $C_1$–$C_4$alkylamino or di($C_1$–$C_4$alkyl)amino;

$R_4$ and $R_5$ together are a group
—C—$R_6(R_7)$—O—C—$R_8(R_9)$—C—$R_{10}(R_{11})$—C—$R_{12}(R_{13})$— ($Z_1$),
—C—$R_{14}(R_{15})$—C—$R_{16}(R_{17})$—O—C—$R_{18}(R_{19})$—C—$R_{20}(R_{21})$— ($Z_2$), or
—C—$R_{22}(R_{23})$—C—$R_{24}(R_{25})$—C—$R_{26}(R_{27})$—O—C—$R_{28}(R_{29})$— ($Z_3$), wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are, each independently of the others, hydrogen, halogen, $C_1$–$C_4$alkyl or $C_1$–$C_4$haloalkyl, it being possible for an alkylene ring, which together with the carbon atoms of the groups $Z_1$, $Z_2$ or $Z_3$ contains from 2 to 6 carbon atoms and which may be interrupted by oxygen, to be either fused or spiro-bound to the carbon atoms of the groups $Z_1$, $Z_2$ or $Z_3$ or that alkylene ring bridges at least one ring atom of the groups $Z_1$, $Z_2$ or $Z_3$;

G is hydrogen, —C($X_1$)—$R_{30}$, —C($X_2$)—$X_3$—$R_{31}$, —C($X_4$)—N($R_{32}$)—$R_{33}$, —SO$_2$—$R_{34}$, an alkali metal, alkaline earth metal, sulfonium or ammonium cation, or —P($X_5$)($R_{35}$)—$R_{36}$ or —CH$_2$—$X_6$—$R_{37}$;

$X_1$, $X_2$, $X_3$, $X_4$, $X_5$ and $X_6$ are, each independently of the others, oxygen or sulfur;

$R_{30}$, $R_{31}$, $R_{32}$ and $R_{33}$ are, each independently of the others, hydrogen, $C_1$–$C_{10}$alkyl, $C_1$–$C_{10}$-haloalkyl, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_{10}$alkoxy-alkyl, $C_4$–$C_{10}$-alkenyloxy-alkyl, $C_4$–$C_{10}$alkynyloxy-alkyl, $C_2$–$C_{10}$alkylthio-alkyl, $C_1$–$C_5$alkysulfoxyl-$C_1$–$C_5$alkyl, $C_1$–$C_5$alkylsulfonyl-$C_1$–$C_5$alkyl, $C_2$–$C_8$alkylideneamino-oxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$aminocarbonyl-$C_1$–$C_5$alkyl, $C_2$–$C_8$dialkyl-aminocarbonyl-$C_1$–$C_5$alkyl, $C_1$–$C_5$alkylcarbonylamino-$C_1$–$C_5$alkyl, $C_2$–$C_5$alkylcarbonyl-($C_1$–$C_5$alkyl)-aminoalkyl, $C_3$–$C_6$trialkylsilyl-$C_1$–$C_5$alkyl, phenyl-$C_1$–$C_5$alkyl, heteroaryl-$C_1$–$C_5$alkyl, phenoxy- $C_1$–$C_5$alkyl, heteroaryloxy-$C_1$–$C_5$alkyl, $C_2$–$C_5$alkenyl, $C_2$–$C_5$haloalkenyl, $C_3$–$C_8$cycloalkyl, phenyl, or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenyl or heteroaryl or heteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted heteroarylamino, diheteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diheteroarylamino, phenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenylamino, diphenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diphenylamino, $C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkylamino, di-$C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted di-$C_3$–$C_7$cycloalkylamino, $C_3$–$C_7$cycloalkoxy or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkoxy;

$R_{34}$, $R_{35}$ and $R_{36}$ are hydrogen, $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_{10}$alkoxy-alkyl, $C_4$–$C_{10}$alkenyloxy-alkyl, $C_4$–$C_{10}$alkynyloxy-alkyl, $C_2$–$C_{10}$alkylthio-alkyl, $C_1$–$C_5$alkysulfoxyl-$C_1$–$C_5$alkyl, $C_1$–$C_5$alkylsulfonyl-$C_1$–$C_5$alkyl, $C_2$–$C_8$alkylideneamino-oxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$aminocarbonyl-$C_1$–$C_5$alkyl, $C_2$–$C_8$dialkylamino-carbonyl-$C_1$–$C_5$alkyl, $C_1$–$C_5$alkylcarbonylamino-$C_1$–$C_5$alkyl, $C_2$–$C_5$alkylcarbonyl-($C_1$–$C_5$alkyl)-aminoalkyl, $C_3$–$C_6$trialkylsilyl-$C_1$–$C_5$alkyl, phenyl-$C_1$–$C_5$alkyl, heteroaryl-$C_1$–$C_5$alkyl, phenoxy-$C_1$–$C_5$alkyl, heteroaryloxy-$C_1$–$C_5$alkyl, $C_2$–$C_5$alkenyl, $C_2$–$C_5$haloalkenyl, $C_3$–$C_8$cycloalkyl, phenyl, or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenyl or heteroaryl or heteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted heteroarylamino, diheteroaryl-amino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diheteroarylamino, phenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenylamino, diphenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diphenylamino, $C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkylamino, di-$C_3$–$C_7$Cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted di-$C_3$–$C_7$cycloalkylamino, $C_3$–$C_7$cycloalkoxy, $C_1$–$C_3$alkyl-, $C_1$–$C_3$haloalkyl-, $C_1$-$C$-$C_3$alkoxy-, $C_1$–$C_3$haloalkoxy-, halo-, cyano- or nitro-substituted $C_3$–$C_7$cycloalkoxy, $C_1$–$C_{10}$alkoxy, $C_1$–$C_{10}$haloalkoxy, $C_1$–$C_5$alkylamino, $C_2$–$C_8$dialkylamino and benzyloxy or phenoxy, it being possible for the benzyl and phenyl groups themselves to be substituted by $C_1$–$C_3$alkyl, $C_1$–$C_3$haloalkyl, $C_1$–$C_3$alkoxy, $C_1$–$C_3$haloalkoxy, halogen, cyano, formyl, acetyl, propionyl, carboxyl, $C_1$–$C_5$alkoxycarbonyl, methylthio, ethylthio or by nitro; and $R_{37}$ is $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_{10}$alkoxy-alkyl, $C_4$–$C_{10}$alkenyloxy-alkyl, $C_4$–$C_{10}$alkynyloxy-alkyl, $C_2$–$C_{10}$alkylthio-alkyl, $C_1$–$C_5$alkysulfoxyl-$C_1$–$C_5$alkyl, $C_1$–$C_5$alkylsulfonyl-$C_1$–$C_5$alkyl, $C_2$–$C_8$alkylideneamino-oxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$aminocarbonyl-$C_1$–$C_5$alkyl, $C_2$–$C_8$dialkylamino-carbonyl-$C_1$–$C_5$alkyl, $C_1$–$C_5$alkylcarbonylamino-$C_1$–$C_5$alkyl, $C_2$–$C_5$alkylcarbonyl-($C_1$–$C_5$alkyl)-aminoalkyl, $C_3$–$C_6$trialkylsilyl-$C_1$–$C_5$alkyl, henyl-$C_1$–$C_5$alkyl, heteroaryl-$C_1$–$C_5$alkyl, phenoxy-$C_1$–$C_5$alkyl, heteroaryloxy-$C_1$–$C_5$alkyl, $C_2$–$C_5$alkenyl, $C_2$–$C_5$haloalkenyl, $C_3$–$C_8$cycloalkyl, phenyl, or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenyl or heteroaryl, or heteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted heteroarylamino, diheteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diheteroarylamino, phenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenylamino, diphenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diphenylamino, $C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkylamino, di-$C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted di-$C_3$–$C_7$Cycloalkylamino, $C_3$–$C_7$cycloalkoxy, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkoxy or $C_1$–$C_{10}$alkylcarbonyl; and salts and diastereoisomers of the compounds of formula I, with the proviso that $R_1$ and $R_3$ are not simultaneously methyl;

b) an amount, which is effective for antagonism of the herbicide, of a safener selected from cloquintocet, an alkali metal, alkaline earth metal, sulfonium or ammonium cation of cloquintocet, or cloquintocet-mexyl, mefenpyr, an alkali metal, alkaline earth metal, sulfonium or ammonium cation of mefenpyr, and mefenpyr-diethyl; and c) an additive comprising an oil of vegetable or animal origin, or a mineral oil, alkyl esters thereof or mixtures of those oils and oil derivatives.

In the above definitions, halogen is to be understood as fluorine, chlorine, bromine or iodine, preferably fluorine, chlorine or bromine. The alkyl groups occurring in the substituent definitions are, for example, methyl, ethyl, n-propyl, isopropyl, n-butyl, sec-butyl, isobutyl or tert-butyl, and the pentyl and hexyl isomers. Suitable cycloalkyl substituents contain from 3 to 6 carbon atoms and are, for example, cyclopropyl, cyclobutyl, cyclopentyl or cyclohexyl. They may be substituted one or more times by halogen, preferably fluorine, chlorine or bromine. Alkenyl is to be understood as, for example, vinyl, allyl, methallyl, 1-methylvinyl or but-2-en-1-yl. Alkynyl is, for example, ethynyl, propargyl, but-2-yn-1-yl, 2-methylbutyn-2-yl or but-3-yn-2-yl. Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl or 2,2,2-trichloroethyl, preferably trichloromethyl, difluorochloromethyl, difluoromethyl, trifluoromethyl or dichlorofluoromethyl. Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_2$–$C_6$alkenyl groups substituted once, twice or three times by halogen preference is given to those having a chain length of from 3 to 5 carbon atoms. Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy, or a pentyloxy or hexyloxy isomer, preferably methoxy or ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl or ethoxycarbonyl. Alkylthio groups preferably have a chain length of from 1 to 4 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl. Alkylamino is, for example, methylamino, ethylamino, n-propylamino, isopropylamino or a butylamine isomer. Dialkylamino is, for example, dimethylamino, methylethylamino, diethylamino, n-propylmethylamino, dibutylamino or diisopropylamino. Alkoxyalkyl groups preferably have from 2 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. Phenyl may be in substituted form, in which case the substituents may be in the ortho-, meta- and/or para-position. Preferred positions for the substituents are the ortho- and para-positions to the ring attachment point. Heteroaryl groups are usually aromatic heterocycles that contain preferably from 1 to 3 hetero atoms selected from nitrogen, oxygen and sulfur. Examples of suitable heterocycles and heteroaromatic compounds are: pyrrolidine, piperidine, pyran, dioxane, azetidine, oxetane, pyridine, pyrimidine, triazine, thiazole, thiadiazole, imidazole, oxazole, isoxazole and pyrazine, furan, morpholine, piperazine, pyrazole, benzoxazole, benzothiazole, quinoxaline and quinoline. Those heterocycles and heteroaromatic compounds may be further substituted, for example by halogen, alkyl, alkoxy, haloalkyl, haloalkoxy, nitro, cyano, thioalkyl, alkylamino or by phenyl. The $C_2$–$C_{10}$-alkenyl- and -alkynyl groups $R_{34}$ may be mono- or poly-unsaturated. They contain preferably from 2 to 12 carbon atoms, especially from 2 to 6 carbon atoms.

Alkali metal, alkaline earth metal or ammonium cations for the substituent G are, for example, the cations of sodium, potassium, magnesium, calcium and ammonium. Preferred sulfonium cations are especially trialkylsulfonium cations wherein the alkyl radicals each contain preferably from 1 to 4 carbon atoms.

The left-hand free valence of the groups $Z_1$, $Z_2$ and $Z_3$ is bound to the 1-position and the right-hand free valence to the 2-position of the pyrazoline ring.

Compounds of formula I wherein it is possible for an alkylene ring, which together with the carbon atoms of the groups $Z_1$, $Z_2$ or $Z_3$ contains from 2 to 6 carbon atoms, to be fused or spiro-bound to the groups $Z_1$, $Z_2$ and $Z_3$ have, for example, the following structure:

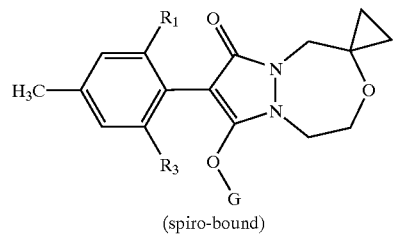

(spiro-bound)

or

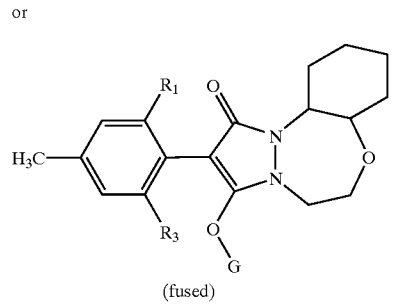

(fused)

Compounds of formula I wherein in the groups $Z_1$, $Z_2$ or $Z_3$ an alkylene ring bridges at least one ring atom of the groups $Z_1$, $Z_2$ or $Z_3$, have, for example, the following structure:

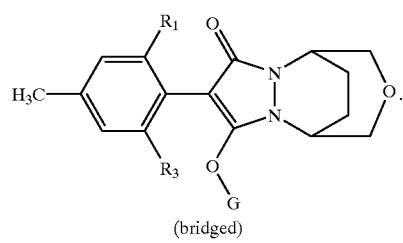

(bridged)

In herbicides of formula I that are preferred for the compositions in accordance with the invention, $R_1$ and $R_3$ are each independently of the other ethyl, haloethyl, ethynyl, $C_1$–$C_2$alkoxy or $C_1$–$C_2$haloalkoxy.

Preference is also given to those compositions in accordance with the invention wherein $R_4$ and $R_5$ together are a $Z_2$ group —C—$R_{14}(R_{15})$—C—$R_{16}(R_{17})$—O—C—$R_{18}(R_{19})$—C—$R_{20}(R_{21})$— ($Z_2$) wherein $R_{14}$, $R_{15}$, $R_{16}$, $R_{17}$, $R_{18}$, $R_{19}$, $R_{20}$ and $R_{21}$ are very especially hydrogen.

In a further preferred group of compositions according to the invention, in formula I $R_{30}$, $R_{31}$, $R_{32}$ and $R_{33}$ are, each independently of the others, hydrogen, $C_1$–$C_8$alkyl, $C_1$–$C_8$haloalkyl, $C_1$–$C_8$cyanoalkyl, $C_1$–$C_8$nitroalkyl, $C_1$–$C_8$aminoalkyl, $C_2$–$C_5$alkenyl, $C_2$–$C_5$haloalkenyl, $C_3$–$C_8$cycloalkyl, $C_1$–$C_5$alkylamino-$C_1$–$C_5$alkyl, $C_2$–$C_8$dialkylamino-$C_1$–$C_5$alkyl, $C_3$–$C_7$cycloalkil-$C_1$–$C_5$alkyl, $C_2$–$C_4$alkoxy-alkyl, $C_4$–$C_6$alkenyloxy-alkyl, $C_4$–$C_6$alkynyloxy-alkyl, $C_2$–$C_4$alkylthio-alkyl, $C_1$–$C_4$alkylsulfinyl-$C_1$–$C_2$alkyl, $C_1$–$C_2$alkylsulfonyl-$C_1$–$C_2$alkyl, $C_2$–$C_4$alkylideneamino-oxy-$C_1$–$C_2$alkyl, $C_1$–$C_5$alkylcarbonyl-$C_1$–$C_2$alkyl, $C_1$–$C_5$alkoxycarbonyl-$C_1$–$C_2$alkyl, $C_1$–$C_5$aminocarbonyl-$C_1$–$C_2$alkyl, $C_2$–$C_8$dialkylamino-carbonyl-$C_1$–$C_2$alkyl, $C_1$–$C_5$alkylcarbonylamino-$C_1$–$C_2$alkyl, $C_2$–$C_5$alkylcarbonyl-($C_1$–$C_2$alkyl)-aminoalkyl, $C_3$–$C_6$trialkylsilyl-$C_1$–$C_5$alkyl, phenyl-$C_1$–$C_2$alkyl, heteroaryl-$C_1$–$C_2$alkyl, phenoxy-$C_1$–$C_2$alkyl, heteroaryloxy-$C_1$–$C_2$alkyl, phenyl or heteroaryl;

$R_{34}$, $R_{35}$ and $R_{36}$, are each independently of the others, hydrogen, $C_1$–$C_8$alkyl, $C_1$–$C_8$haloalkyl, $C_1$–$C_8$cyanoalkyl, $C_1$–$C_8$nitroalkyl, $C_1$–$C_8$aminoalkyl, $C_2$–$C_5$alkenyl, $C_2$–$C_5$haloalkenyl, $C_3$–$C_8$cycloalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_4$alkoxy-alkyl, $C_4$–$C_6$alkenyloxy-alkyl, $C_4$–$C_6$alkynyloxy-alkyl, $C_2$–$C_4$alkylthio-alkyl, $C_1$–$C_4$alkylsulfinyl-$C_1$–$C_2$alkyl, $C_1$–$C_2$alkylsulfonyl-$C_1$–$C_2$alkyl, $C_2$–$C_4$alkylideneamino-oxy-$C_1$–$C_2$alkyl, $C_1$–$C_5$alkylcarbonyl-$C_1$–$C_2$alkyl, $C_1$–$C_5$alkoxycarbonyl-$C_1$–$C_2$alkyl, $C_1$–$C_5$aminocarbonyl-$C_1$–$C_2$alkyl, $C_2$–$C_8$dialkylamino-carbonyl-$C_1$–$C_2$alkyl, $C_1$–$C_5$alkylcarbonylamino-$C_1$–$C_2$alkyl, $C_2$–$C_5$alkylcarbonyl-($C_1$–$C_2$alkyl)-aminoalkyl, $C_3$–$C_6$trialkylsilyl-$C_1$–$C_5$alkyl, phenyl-$C_1$–$C_2$alkyl, heteroaryl-$C_1$–$C_2$alkyl, phenoxy-$C_1$–$C_2$alkyl, heteroaryloxy-$C_1$–$C_2$alkyl, phenyl or heteroaryl, benzyloxy or phenoxy, it being possible for the benzyl and phenyl groups themselves to be substituted by halogen, nitro, cyano, amino, dimethylamino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl; and $R_{37}$ is $C_1$–$C_8$alkyl, $C_1$–$C_8$haloalkyl, $C_1$–$C_8$cyanoalkyl, $C_1$–$C_8$nitroalkyl, $C_1$–$C_8$aminoalkyl, $C_2$–$C_5$alkenyl, $C_2$–$C_5$haloalkenyl, $C_3$–$C_8$cycloalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_4$alkoxy-alkyl, $C_4$–$C_6$alkenyloxy-alkyl, $C_4$–$C_6$alkynyloxy-alkyl, $C_2$–$C_4$alkylthio-alkyl, $C_1$–$C_4$alkylsulfinyl-$C_1$–$C_2$alkyl, $C_1$–$C_2$alkylsulfonyl-$C_1$–$C_2$alkyl, $C_2$–$C_4$alkylideneamino-oxy-$C_1$–$C_2$alkyl, $C_1$–$C_5$alkylcarbonyl-$C_1$–$C_2$alkyl, $C_1$–$C_5$alkoxycarbonyl-$C_1$–$C_2$alkyl, $C_1$–$C_5$aminocarbonyl-$C_1$–$C_2$alkyl, $C_2$–$C_8$dialkylamino-carbonyl-$C_1$–$C_2$alkyl, $C_1$–$C_5$alkylcarbonylamino-$C_1$–$C_2$alkyl, $C_2$–$C_5$alkylcarbonyl-($C_1$–$C_2$alkyl)-aminoalkyl, $C_3$–$C_6$trialkylsilyl-$C_1$–$C_5$alkyl, phenyl-$C_1$–$C_2$alkyl, heteroaryl-$C_1$–$C_2$alkyl, phenoxy-$C_1$–$C_2$alkyl, heteroaryloxy-$C_1$–$C_2$alkyl, phenyl or heteroaryl, benzyloxy or phenoxy, it being possible for the benzyl and phenyl groups themselves to be substituted by halogen, nitro, cyano, amino, dimethylamino, hydroxy, methoxy, ethoxy, methylthio, ethylthio, formyl, acetyl, propionyl, carboxyl, $C_1$–$C_2$alkoxycarbonyl or by $C_1$- or $C_2$-haloalkyl; or $R_{37}$ is $C_1$–$C_8$alkylcarbonyl.

Special preference is given to those compositions according to the invention wherein, in formula I, $R_{30}$, $R_{31}$, $R_{32}$ and $R_{33}$ are, each independently of the others, hydrogen, $C_1$–$C_8$alkyl, $C_1$–$C_8$haloalkyl, $C_2$–$C_5$alkenyl, $C_2$–$C_5$haloalkenyl, $C_3$–$C_8$cycloalkyl, $C_3$–$C_7$cycloalkyl, $C_2$–$C_4$alkoxy-alkyl, phenyl, heteroaryl, phenyl-$C_1$–$C_2$alkyl, heteroaryl-$C_1$–$C_2$alkyl, phenoxy-$C_1$–$C_2$alkyl, heteroaryloxy-$C_1$–$C_2$alkyl;

$R_{34}$, $R_{35}$ and $R_{36}$ are, each independently of the others, hydrogen, $C_1$–$C_8$alkyl, $C_1$–$C_8$haloalkyl, $C_2$–$C_5$alkenyl, $C_2$–$C_5$haloalkenyl, $C_3$–$C_8$cycloalkyl, $C_3$–$C_7$cycloalkyl-$C_1$–$C_2$alkyl, $C_{2-C_4}$alkyl, phenyl, heteroaryl, phenyl-$C_1$–$C_2$alkyl, heteroaryl-$C_1$–$C_2$alkyl, phenoxy-$C_1$–$C_2$alkyl, heteroaryloxy-$C_1$–$C_2$alkyl, $C_1$–$C_6$alkoxy, $C_1$–$C_3$alkylamino or di($C_1$–$C_3$alkyl) amino; and $R_{37}$ is $C_1$–$C_8$alkyl, $C_1$–$C_8$haloalkyl, $C_2$–$C_5$alkenyl, $C_2$–$C_5$haloalkenyl, $C_3$–$C_8$cycloalkyl, $C_3$–$C_7$cycloalkyl-$C_1$–$C_2$alkyl, $C_2$–$C_4$alkoxy-alkyl, phenyl, heteroaryl, phenyl-$C_1$–$C_2$alkyl, heteroaryl-$C_1$–$C_2$alkyl, phenoxy-$C_1$–$C_2$alkyl, heteroaryloxy-$C_1$–$C_2$alkyl, $C_1$–$C_6$alkoxy, $C_1$–$C_3$alkylamino, di-($C_1$–$C_3$alkyl)-amino or $C_1$–$C_8$alkylcarbonyl.

An especially preferred safener in the composition according to the invention is cloquintocet-mexyl. As a suitable oil additive, special emphasis should be given within the context of the invention to MERGE® and Actiprom®.

The compositions according to the invention may also comprise salts that the compounds of formula I may form with acids. Suitable acids for the formation of acid addition salts are both organic and inorganic acids. Examples of such acids are hydrochloric acid, hydrobromic acid, nitric acid, phosphoric acids, sulfuric acid, acetic acid, propionic acid, butyric acid, valeric acid, oxalic acid, malonic acid, fumaric acid, organic sulfonic acids, lactic acid, tartaric acid, citric acid and salicylic acid. The salts of the compounds of formula I having acid hydrogen also are alkali metal salts, for example sodium and potassium salts; alkaline earth metal salts, for example calcium and magnesium salts; ammonium salts, that is to say unsubstituted ammonium salts and mono- or poly-substituted ammonium salts, or are salts with other organic nitrogen bases. Suitable salt formers are accordingly alkali metal and alkaline earth metal hydroxides, especially the hydroxides of lithium, sodium, potassium, magnesium or calcium, with those of sodium or potassium being given special importance.

Examples of suitable amines for ammonium salt formation that come into consideration are ammonia as well as primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butyl-ethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, N-methylmorpholine, thio-morpholine, piperidine, pyrrolidine, indoline, quinuclidine and azepine; primary aryl amines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

If non-chiral starting materials are employed, the asymmetrically substituted compounds of formula I obtained in the processes described in this Application are generally in the form of racemates. The stereoisomers can then be separated on the basis of their physicochemical properties according to known methods, such as, for example, fractional crystallisation following salt formation with optically pure bases, acids or metal complexes, or by chromatographic procedures, such as, for example, high-pressure liquid chromatography (HPLC) on acetyl cellulose. In the present invention, "compounds of formula I" are to be understood as including both the concentrated and optically pure forms of the stereoisomers in question and the racemates and diastereoisomers. Where no special mention is made of individual optical antipodes, the formula in question is to be understood as referring to the racemic mixtures that are obtained in the preparation process mentioned. When an aliphatic C=C double bond is present, geometric isomerism may also occur.

The compounds of formula I may, also in dependence upon the nature of the substituents, occur as geometric and/or optical isomers and isomeric mixtures and as tautomers and tautomeric mixtures. For example, the compounds of formula I wherein the group G is hydrogen can occur in the following tautomeric equilibria:

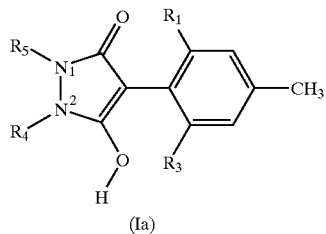

(Ia)

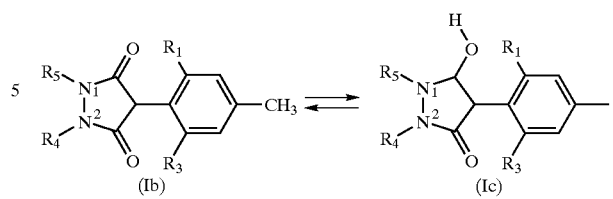

(Ib)    (Ic)

When G is other than hydrogen and Z is the group $Z_1$ or $Z_3$, or when G is other than hydrogen and $Z_2$ is asymmetrically substituted, fused or spiro-bounded, the compound of formula I may occur as an isomer of formula Id

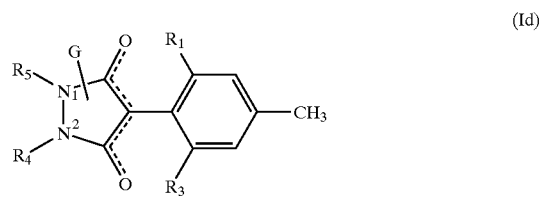

(Id)

Processes for the preparation of compounds that differ from the compounds of formula I according to the present invention in respect of the meanings of the substituents $R_4$ and $R_5$ are described, for example, in WO 96/21652. The compounds of formula I according to the present invention can be prepared analogously to the processes described in WO 96/21652.

The compounds of formula II

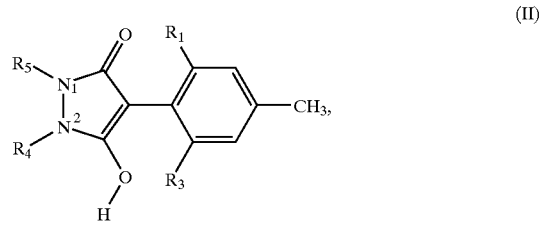

(II)

wherein $R_1$, $R_3$, $R_4$ and $R_5$ are as defined for formula I, used as starting materials for such processes can be prepared, for example, by reacting a compound of formula III

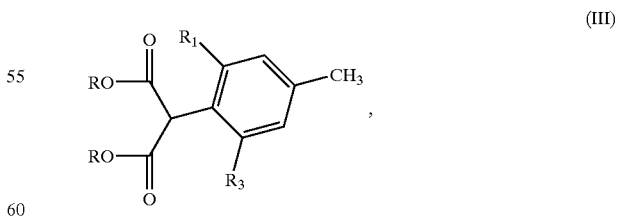

(III)

wherein R is $C_1$–$C_6$alkyl, $C_1$–$C_6$haloalkyl, preferably methyl, ethyl or trichloroethyl and $R_1$ and $R_3$ are as defined for formula I, in an inert organic solvent, optionally in the presence of a base, with a compound of formula IV or IVa

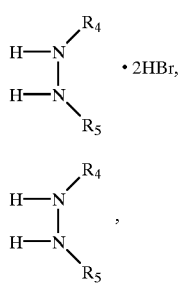

wherein $R_4$ and $R_5$ are as defined for formula I. Further preparation processes leading to compounds of formula II are also described, for example, in WO 92/16510.

The compounds of formula III either are known or can be prepared analogously to known processes. Processes for the preparation of compounds of formula III and the reaction thereof with hydrazines are described, for example, in WO 97/02243. Compounds of formula III wherein R is $C_1$–$C_6$alkyl, $C_1$–$C_6$haloalkyl, preferably methyl, ethyl or trichloroethyl and $R_1$, $R_2$ and $R_3$ are as defined for formula I can be prepared analogously to methods known to the person skilled in the art. For example, compounds of formula III wherein R is $C_1$–$C_6$alkyl or $C_1$–$C_6$haloalkyl, preferably methyl, ethyl or trichloroethyl and $R_1$, $R_2$ and $R_3$ are each independently of the others, $C_1$–$C_4$alkyl, $C_2$–$C_4$alkenyl or $C_2$–$C_4$alkynyl can be prepared according to the process of cross-coupling according to Stille (J. K. Stille, Angew. Chem. 1986, 98, 504–519), Sonogashira (K. Sonogashira et al., Tetrahedron Lett. 1975, 4467–4470), Suzuki (N. Miyaura, A. Suzuki, Chem. Rev. 1995, 95, 2457–2483) or Heck (R. F. Heck, Org. React. 1982, 27, 345–390) and, optionally, subsequent hydrogenation. The following Reaction Scheme illustrates this procedure:

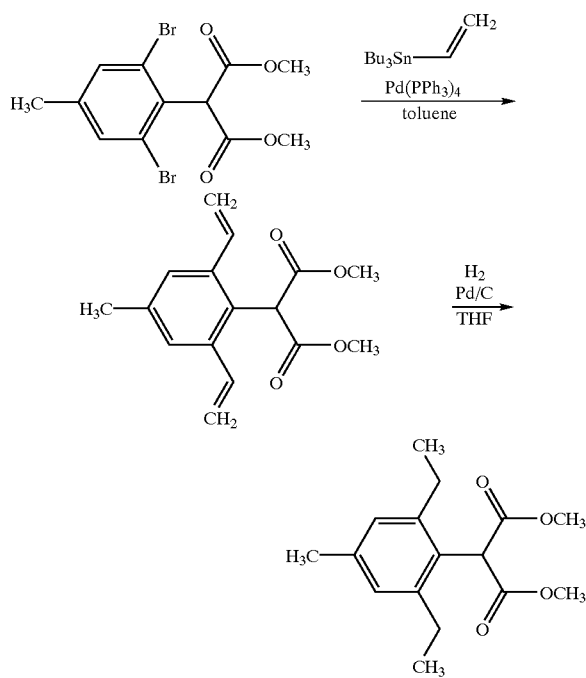

The compounds of formulae IV and IVa either are known or can be prepared analogously to known processes. Processes for the preparation of compounds of formula IV are described, for example, in WO 95/00521. Those compounds can be prepared, for example, by heating a compound of formula V

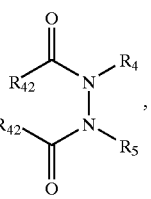

wherein $R_{42}$ is hydrogen, $C_1$–$C_4$alkyl, $C_1$–$C_6$alkoxy, $C_1$–$C_6$haloalkoxy or benzyloxy, preferably hydrogen, methyl, methoxy, ethoxy, trichloroethoxy, tert-butoxy or benzyloxy and $R_4$ and $R_5$ are as defined for formula I, in an inert solvent in the presence of a base or acid. Compounds of formula V wherein $R_{42}$ is hydrogen, $C_1$–$C_4$alkyl, $C_1$–$C_6$alkoxy, $C_1$–$C_6$haloalkoxy or benzyloxy, preferably hydrogen, methyl, methoxy, ethoxy, trichloroethoxy, tert-butoxy or benzyloxy and $R_4$ and $R_5$ are as defined for formula I can be prepared, for example by reacting a compound of formula VI

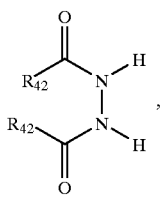

wherein $R_{42}$ is hydrogen, $C_1$–$C_4$alkyl, $C_1$–$C_6$alkoxy, $C_1$–$C_6$haloalkoxy or benzyloxy, preferably hydrogen, methyl, methoxy, ethoxy, trichloroethoxy, tert-butoxy or benzyloxy, in the presence of a base and an inert solvent, with a compound of formula VII $$Y\text{-}\{Z_1, Z_2, \text{or } Z_3\}\text{-} \tag{VII}$$

wherein Y is halogen, alkyl/aryl sulfonate —$OSO_2R_{43}$, preferably bromine, chlorine, iodine, mesylate ($R_{43}$=$CH_3$), triflate ($R_{43}$=$CF_3$) or tosylate ($R_{43}$=p-tolyl) and $Z_1$, $Z_2$, and $Z_3$ are as defined for formula I. In formula VII, the free valences of the groups $Z_1$, $Z_2$, and $Z_3$ are in each case bound to the group Y. Compounds of formula VI and VII are known or can be prepared analogously to methods known to the person skilled in the art.

Compounds of formula IV wherein $R_4$ and $R_5$ together are a group $Z_2$ —C—$R_{14}$($R_{15}$)—C—$R_{16}$($R_{17}$)—O—C—$R_{18}$($R_{19}$)—C—$R_{20}$($R_{21}$)— ($Z_2$) wherein $R_{14}$, $R_{15}$, $R_{16}$, $R_{17}$, $R_{18}$, $R_{19}$, $R_{20}$ and $R_{21}$ are hydrogen can be prepared, for example, in accordance with the following Reaction Scheme:

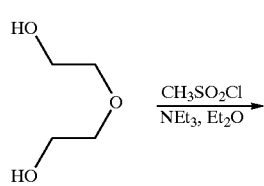

-continued

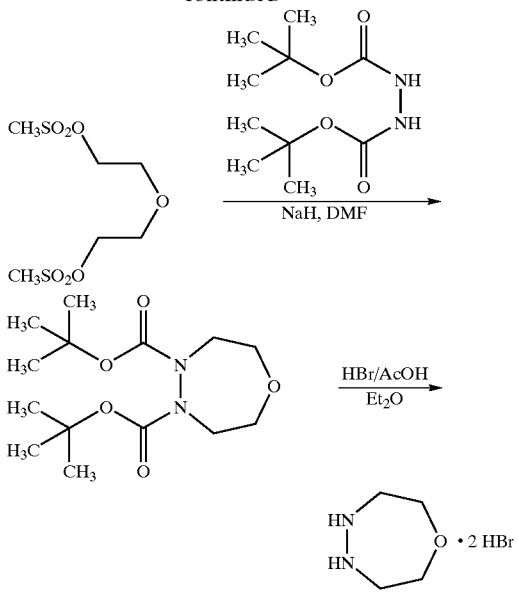

HBr/AcOH
―――――→
Et₂O

PREPARATION EXAMPLES

Example P1

Preparation of:

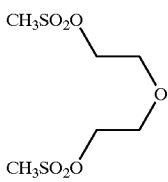
(1)

A solution of 177.6 g of methanesulfochloride in 400 ml of diethyl ether is added dropwise over the course of one hour to a solution, cooled to −10° C., of 80.6 g (0.76 mol) of diethylene glycol and 159.9 g (1.58 mol) of triethylamine in 1500 ml of diethyl ether, the temperature being maintained below 5° C. After stirring for 30 minutes at a temperature of 0° C., the cooling is removed. After 2 hours, 12 ml of triethylamine and 12 ml of methanesulfochloride are added at a temperature of 20° C. and stirring is carried out for a further 4 hours. The resulting white suspension is then transferred to a suction filter and the residue is washed twice with 300 ml of diethyl ether. The filter residue is taken up in 2000 ml of ethyl acetate and the suspension is stirred for 30 minutes at room temperature and filtered again. The filtrate obtained is concentrated by evaporation and the residue is used in the next reaction without further purification. 216.5 g of the desired crude product (1) are obtained in the form of white crystals.

The end products of formula I can be isolated in conventional manner by concentrating and/or evaporating off the solvent and by recrystallising or triturating the solid residue in solvents in which they are not readily soluble, such as ethers, alkanes, aromatic hydrocarbons or chlorinated hydrocarbons, or they can be purified by means of chromatography. Salts of compounds of formula I can be prepared in a manner known per se. Such preparation methods are described, for example, in WO 96/21652.

Example P2

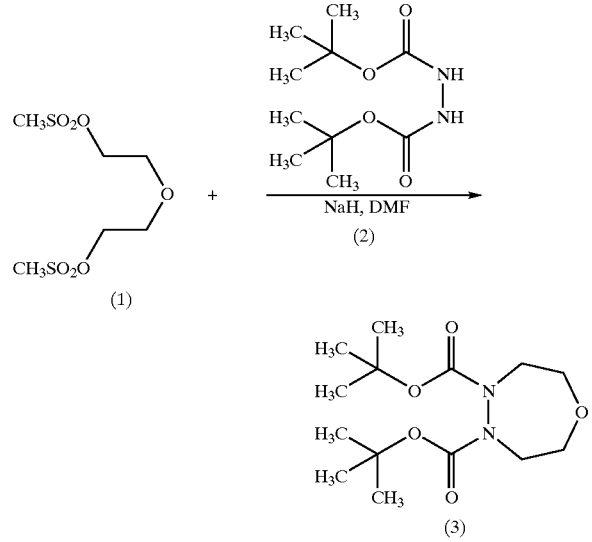

A solution of 68.78 g (0.30 mol) of (2) in 140 ml of dimethylformamide is added dropwise over the course of 30 minutes to a suspension, cooled to 5° C., of 23.9 g (0.60 mol) of 60% sodium hydride in 500 ml of dimethylformamide. The cooling is removed and stirring is carried out until the reaction mixture has reached a temperature of 20° C. The mixture is then heated briefly to a temperature of from 30 to 40° C. in order to complete the elimination of hydrogen. After cooling to a temperature of from 0 to 5° C., a solution of 80 g (0.305 mol) of (1) in 160 ml of dimethylformamide is added dropwise over the course of 30 minutes, the temperature being maintained at from 0 to 5° C. After removing the cooling, and stirring for 3 hours at room temperature and for 45 minutes at about 40° C., the reaction mixture is poured onto a mixture of saturated ammonium chloride solution, ice and tert-butyl methyl ether; the phases are separated and the organic phase is then washed with water (twice). After drying the organic phase with sodium sulfate, concentration by evaporation and further drying at a temperature of 40° C. in vacuo, 92.2 g of (3) are obtained in the form of a light-yellow oil. The crude product is used in the next reaction without further purification.

Example P3

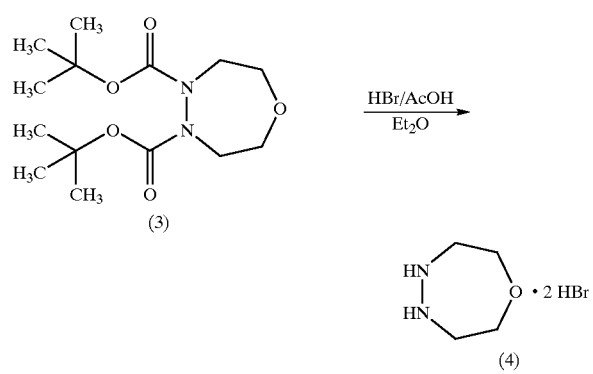

160.5 ml of a 33% solution of hydrogen bromide in glacial acetic acid are added dropwise, over the course of 30 minutes, to a solution, cooled to 0° C., of 92.2 g (0.305 mol) of (3) in 1200 ml of diethyl ether. After removing the cooling and then stirring for 22 hours at 20° C. and stirring for 27 hours under reflux, the resulting white suspension is transferred to a suction filter; subsequent washing with diethyl ether is carried out and the filter residue is then dried over $P_2O_5$ in vacuo at a temperature of from 50 to 60° C. The product (4) is obtained in a yield of 52.9 g in the form of a white solid.

Example P4

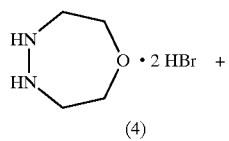

(4)

and degassing is carried out (4× vacuum/argon). The yellow suspension is then heated to a temperature of 60° C. and stirred for 3 hours. 5.07 g (16.5 mmol) of (5) are then added and heating is carried out at a bath temperature of 140° C. in order to distil off in continuous manner excess triethylamine and the ethanol that is formed. After 3 hours, the reaction mixture is cooled to a temperature of 40° C. and is poured into 100 ml of an ice/water mixture. The reaction mixture is rendered alkaline using aqueous 1 N sodium hydroxide solution and the aqueous phase (containing the product) is washed twice with ethyl acetate. After then washing the organic phase twice with aqueous 1 N sodium hydroxide solution, the aqueous phases are combined, the remaining xylene is distilled off and the combined aqueous phases are adjusted to pH 2–3 using 4N HCl, with cooling. The product that is then precipitated is transferred to a suction filter, the filter residue is washed with water and briefly with hexane and the filter residue is then dried in vacuo at a temperature of 60° C. over $P_2O_5$. 4.08 g of solid (6) having a melting point of 189–191 ° C. (decomp.) are obtained.

Example P5

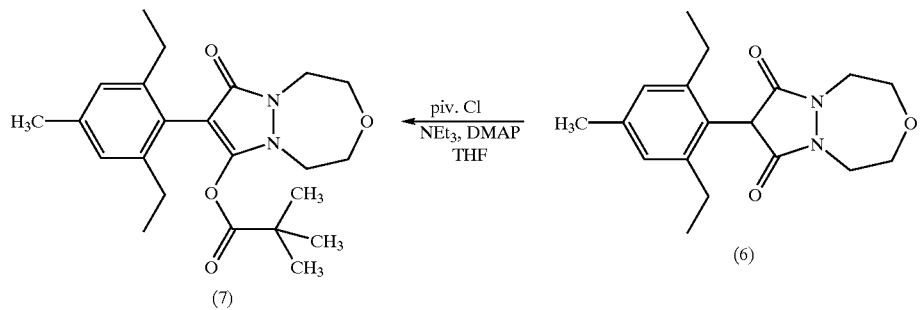

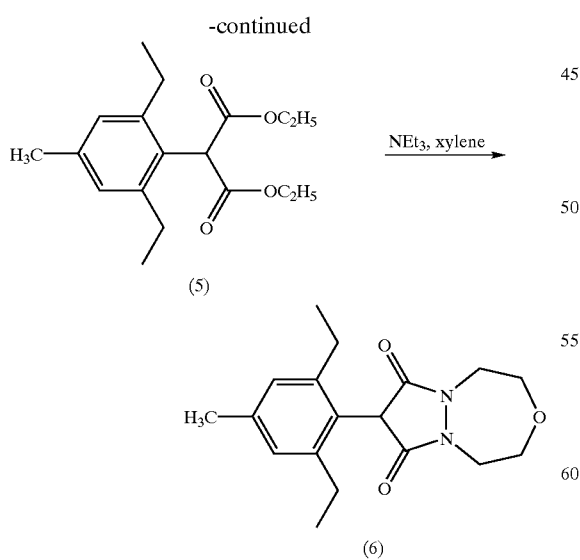

10.61 ml (76 mmol) of triethylamine are added to a suspension of 4.4 g (16.5 mmol) of (4) in 175 ml of xylene A catalytic amount of 4-dimethylaminopyridine is added to a solution, cooled to a temperature of 0° C., of 1 g (3.2 mmol) of (6) and 0.65 g (6.4 mmol) of triethylamine in 30 ml of tetrahydrofuran. 0.49 g (4.1 mmol) of pivaloyl chloride is then added dropwise. After stirring for 30 minutes at a temperature of 0° C., the cooling is removed and stirring is carried out for a further 60 minutes. The reaction mixture is then poured into saturated aqueous sodium chloride solution and the organic phase is separated off. The organic phase is dried over magnesium sulfate, filtered and concentrated by evaporation. After chromatographic purification and recrystallisation from diethyl ether, 1.07 g of (7) having a melting point of from 122 to 123° C. are obtained.

Example P6

Preparation of

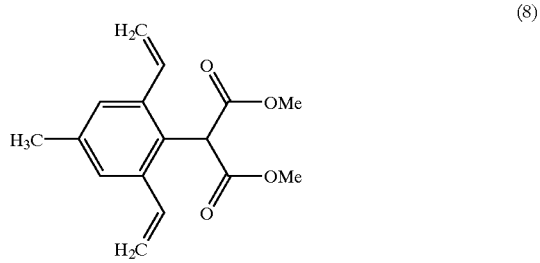

To a solution of 20 g of 2-(2,6-dibromo-4-methyl-phenyl)-malonic acid dimethyl ester (known from WO 96/35664) (52.6 mmol) in 400 ml of toluene (degassed 3 times, vacuum/argon) there are added first 36.7 g (0.116 mol) of tributylvinylstannane and then 2 g of tetrakis-(triphenylphosphine)palladium. The reaction mixture is then stirred for 9 hours at a temperature of from 90 to 95° C. After filtering over Hyflo and concentrating using a rotary evaporator, 15.3 g of (8) are obtained, after chromatographic purification, in the form of a yellow oil which is used in the next reaction without further purification.

Example P7

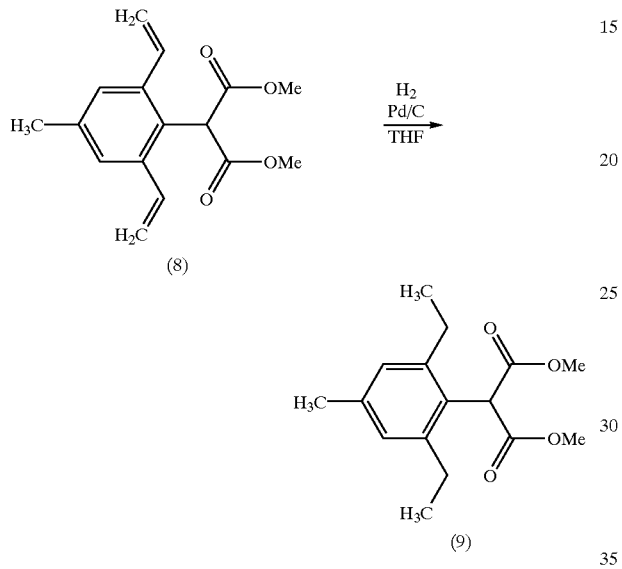

15.2 g of the compound (8) obtained in accordance with Example P6 are hydrogenated using hydrogen over a palladium catalyst (carbon as carrier, 7 g of 5% Pd/C) in 160 ml of tetrahydrofuran at a temperature of from 20 to 25° C. After the hydrogenation is complete, the product is filtered over Hyflo and the filtrate obtained is concentrated using a rotary evaporator. 13.7 g of (5) are obtained in the form of yellow crystals having a melting point of from 47 to 49° C.

Example P8

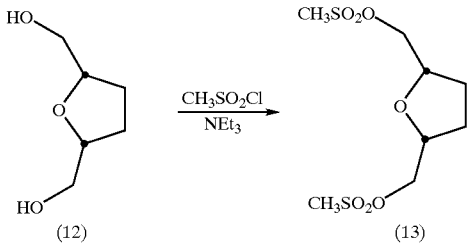

67.8 g (0.59 mol) of methanesulfochloride are added dropwise to a solution, cooled to 0–3° C., of 37.1 g (0.28 mol) of cis-2,5-bis(hydroxymethyl)tetrahydrofuran (12) and 65.3 g (0.65 mol) of triethylamine in 400 ml of methylene chloride, the temperature being maintained below 7° C. Stirring is then carried out overnight at a temperature of 20° C. The resulting white suspension is transferred to a suction filter, the residue is washed with methylene chloride no and the filtrate is concentrated by evaporation. The residue is taken up in ethyl acetate, washed with water (twice) and with saturated aqueous sodium chloride solution (once), dried (Na$_2$SO$_4$) and concentrated. 72.7 g of the dimesylate compound (13) are obtained in the form of a crude oil which is used in the next reaction without further purification. The starting material (12) is known in the literature: see, for example, K. Naemura et al., Tetrahedron Asymmetry 1993, 4, 911–918.

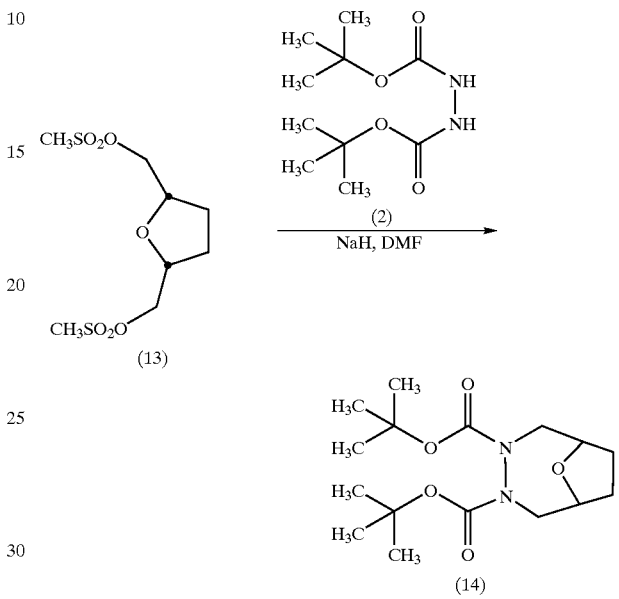

Example P9

Analogously to Preparation Example P2, starting from 21.0 9 (0.53 mol) of 60% NaH, 58.4 g (0.25 mol) of (2) and 72.5 g (0.25 mol) of dimesylate (13) in a total of 840 ml of dimethylformamide, (14) is obtained in the form of a crude brown oil. After chromatographic purification, 53.7 g of the pure compound (14) are obtained in the form of a white solid having a melting point of from 81 to 83° C.

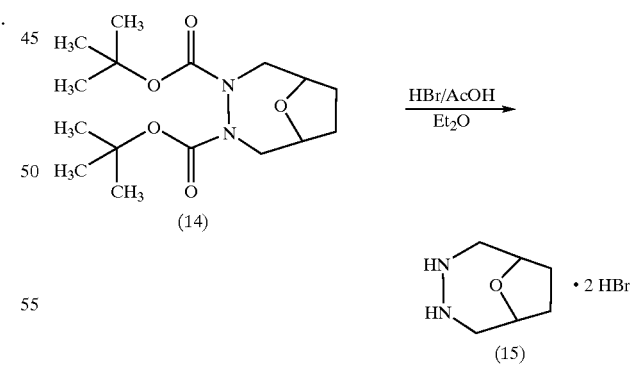

Example P10

Analogously to Preparation Example P3, starting from 53.5 g (0.16 mol) of (14) in 800 ml of diethyl ether and 90 ml of a 33% solution of hydrogen bromide in concentrated acetic acid, 36.5 g of the bicyclic hydrazine (15) are obtained in the form of a solid having a melting point of from 262 to 264° C.

Example P11

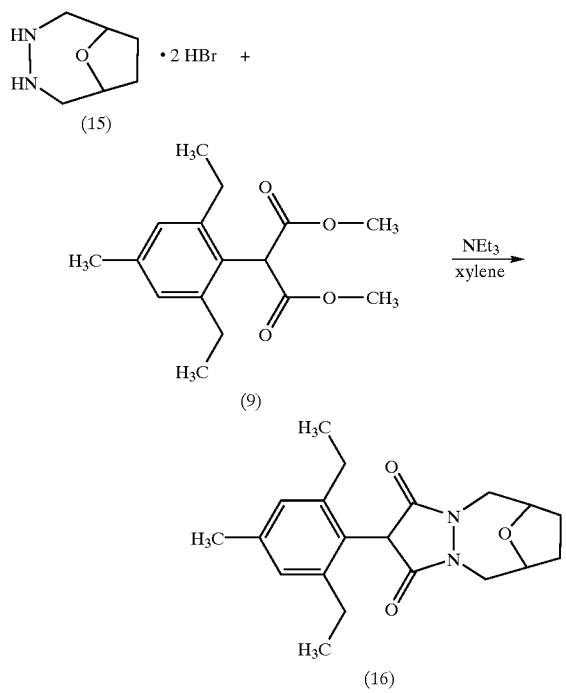

Analogously to Preparation Example P4, starting from 0.105 mol of the malonate (9) and 30.4 g (0.105 mol) of the hydrazine (15), 29.7 g of the compound (16) are obtained in the form of a solid having a melting point of 287° C.

Example P12

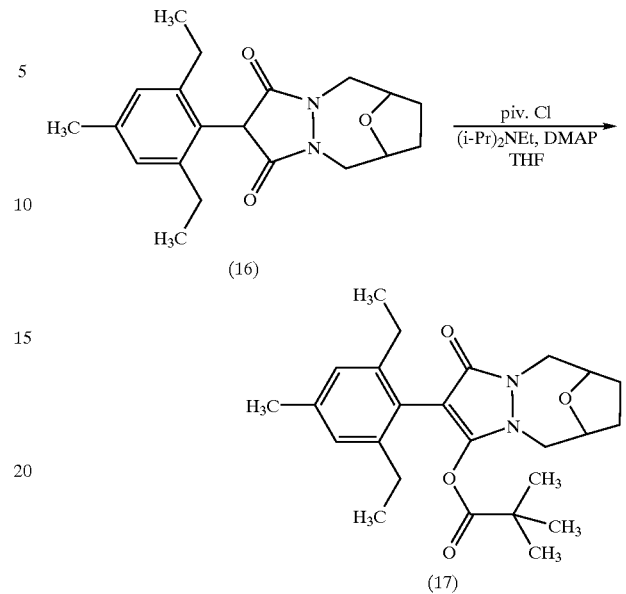

Analogously to Preparation Example P9, starting from 1.1 g (3.2 mmol) of (16), 0.83 g of the pivaloyl ester (17) is obtained in the form of a solid having a melting point of 141–143° C.

In the Table that follows, where a formula is shown for the substituent G, the left-hand side of the formula is the point of attachment to the oxygen atom of the heterocycle. The other terminal valences represent methyl groups. Melting points are given in ° C.

TABLE 1

Compounds of formula Ie:
Error! Objects cannot be created from editing field codes.
(Ie)

| Comp. no. | $R_1$ | $R_3$ | G | physical data |
|---|---|---|---|---|
| 1.001 | $CH_3$ | $OCH_3$ | H | |
| 1.002 | $CH_3$ | $OCH_3$ | $C(O)C(CH_3)_3$ | |
| 1.003 | $CH_3$ | $OCH_3$ | $C(O)OCH_2CH_3$ | |
| 1.004 | $CH_2CH_3$ | $CH_3$ | H | m.p. 182–185° C. |
| 1.005 | $CH_2CH_3$ | $CH_3$ | $C(O)C(CH_3)_3$ | m.p. 110–113° C. |
| 1.006 | $CH_2CH_3$ | $CH_3$ | $C(O)OCH_2CH_3$ | |
| 1.007 | $CH_2CH_3$ | $CH_2CH_3$ | H | m.p. 189–191° C. |
| 1.008 | $CH_2CH_3$ | $CH_2CH_3$ | $C(O)C(CH_3)_3$ | m.p. 122–124° C. |
| 1.009 | $CH_2CH_3$ | $CH_2CH_3$ | $C(O)OCH_2CH_3$ | m.p. 114–116° C. |
| 1.010 | $CH=CH_2$ | $CH_3$ | H | m.p. 165–170° C. |
| 1.011 | $CH=CH_2$ | $CH_3$ | $C(O)C(CH_3)_3$ | m.p. 111–113° C. |
| 1.012 | $CH=CH_2$ | $CH_2CH_3$ | H | |
| 1.013 | $CH=CH_2$ | $CH=CH_2$ | H | |
| 1.014 | $CH=CH_2$ | $CH=CH_2$ | $C(O)C(CH_3)_3$ | |
| 1.015 | $C\equiv CH$ | $CH_3$ | H | m.p. 179–184° C. |
| 1.016 | $C\equiv CH$ | $CH_3$ | $C(O)C(CH_3)_3$ | m.p. 109–111° C. |
| 1.017 | $C\equiv CH$ | $CH_3$ | $C(O)OCH_2CH_3$ | |
| 1.018 | $C\equiv CH$ | $CH_2CH_3$ | H | m.p. 189–193° C. |
| 1.019 | $C\equiv CH$ | $CH_2CH_3$ | $C(O)C(CH_3)_3$ | |
| 1.020 | $C\equiv CH$ | $CH_2CH_3$ | $C(O)OCH_2CH_3$ | |
| 1.021 | $C\equiv CH$ | $C\equiv CH$ | H | m.p. 300° C. |
| 1.022 | $C\equiv CH$ | $C\equiv CH$ | $C(O)C(CH_3)_3$ | m.p. 183–185° C. |
| 1.023 | $C\equiv CH$ | $C\equiv CH$ | $C(O)OCH_2CH_3$ | |
| 1.024 | $C\equiv CH$ | $CH=CH_2$ | H | |
| 1.025 | $C\equiv CCH_3$ | $CH_3$ | H | m.p. 179–181° C. |
| 1.026 | $C\equiv CCH_3$ | $CH_3$ | $C(O)C(CH_3)_3$ | m.p. 128–129° C. |
| 1.027 | $C\equiv CCH_3$ | $CH_3$ | $C(O)OCH_2CH_3$ | |
| 1.028 | $C\equiv CCH_3$ | $CH_2CH_3$ | H | |
| 1.029 | $C\equiv CCH_3$ | $CH_2CH_3$ | $C(O)C(CH_3)_3$ | |

TABLE 1-continued

Compounds of formula Ie:
Error! Objects cannot be created from editing field codes.
(Ie)

| Comp. no. | R₁ | R₃ | G | physical data |
|---|---|---|---|---|
| 1.030 | C≡CCH₃ | C≡CCH₃ | H | |
| 1.031 | C≡CCH₃ | C≡CCH₃ | C(O)C(CH₃)₃ | |
| 1.032 | CH₂CH₂CH₃ | CH₃ | H | m.p. 136–138° C. |
| 1.033 | CH₂CH₂CH₃ | CH₃ | C(O)C(CH₃)₃ | m.p. 65–67° C. |
| 1.034 | CH₂CH₂CH₃ | CH₃ | C(O)OCH₂CH₃ | |
| 1.035 | CH₂CH₂CH₃ | CH₂CH₃ | H | |
| 1.036 | CH₂CH₂CH₃ | CH₂CH₂CH₃ | H | |
| 1.037 | CH₂CH₂CH₃ | CH₂CH₂CH₃ | C(O)C(CH₃)₃ | |
| 1.038 | CH₂CH₂CH₃ | CH₂CH₂CH₃ | C(O)OCH₂CH₃ | |
| 1.039 | CH₂CH₂CH₃ | C≡CH | H | |
| 1.040 | CH(CH₃)₂ | CH₃ | H | m.p. 214–216° C. |
| 1.041 | CH(CH₃)₂ | CH₃ | C(O)C(CH₃)₃ | m.p. 148–151° C. |
| 1.042 | CH(CH₃)₂ | CH₂CH₃ | H | |
| 1.043 | CH(CH₃)₂ | C≡CH | H | |
| 1.044 | cyclopropyl | CH₃ | H | |
| 1.045 | cyclopropyl | CH₂CH₃ | H | |
| 1.046 | cyclopropyl | C≡CH | H | |
| 1.047 | CH₂CH=CH₂ | CH₃ | H | |
| 1.048 | CH₂CH=CH₂ | CH₂CH₃ | H | |
| 1.049 | CH₂CH=CH₂ | C≡CH | H | |
| 1.050 | CH₂CH₂CH₂CH₃ | CH₃ | H | |
| 1.051 | CH₃O— | CH₂CH₃ | H | |
| 1.052 | CH₃O— | CH₂CH₃ | C(O)C(CH₃)₃ | |
| 1.055 | CH₂CH₃ | CH₂CH₃ | SO₂CH(CH₃)₂ | |
| 1.054 | CH₂CH₃ | CH₂CH₃ | SO₂CH₃ | crystalline |
| 1.055 | CH₂CH₃ | CH₂CH₃ | SO₂CH(CH₃)₂ | |
| 1.056 | CH₂CH₃ | CH₂CH₃ | SO₂CF₃ | |
| 1.057 | CH₂CH₃ | CH₂CH₃ | SO₂CH₂CH₃ | |
| 1.058 | CH₂CH₃ | CH₂CH₃ | SO₂CH₂CH(CH₃)₂ | wax |
| 1.059 | CH₂CH₃ | CH₂CH₃ | SO₂CH₂CH₂Cl | |
| 1.060 | CH₂CH₃ | CH₂CH₃ | SO₂CH=CH₂ | wax |
| 1.061 | CH₂CH₃ | CH₂CH₃ | SO₂CH₂CH₂Br | |
| 1.062 | CH₂CH₃ | CH₂CH₃ | 4-(methylsulfonyl)-2,1,3-benzoxadiazole | m. p.: 204–205 |
| 1.063 | CH₂CH₃ | CH₂CH₃ | 4-(methylsulfonyl)-2,1,3-benzothiadiazole | m.p.: 203–204 |
| 1.064 | CH₂CH₃ | CH₂CH₃ | SO₂-benzyl | mp.: 157–158 |
| 1.065 | CH₂CH₃ | CH₂CH₃ | SO₂CH₂C(CH₃)=CH₂ | wax |
| 1.066 | CH₂CH₃ | CH₂CH₃ | SO₂CH₂CH₂CH₂Cl | wax |

TABLE 1-continued

Compounds of formula Ie:
Error! Objects cannot be created from editing field codes.
(Ie)

| Comp. no. | $R_1$ | $R_3$ | G | physical data |
|---|---|---|---|---|
| 1.067 | $CH_2CH_3$ | $CH_2CH_3$ | 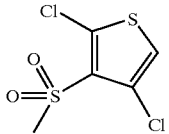 | m.p.: 126 |
| 1.068 | $CH_2CH_3$ | $CH_2CH_3$ | 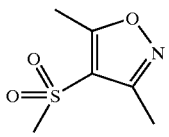 | m.p.: 146 |
| 1.069 | $CH_2CH_3$ | $CH_2CH_3$ | 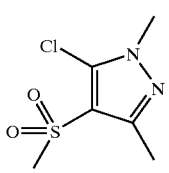 | m.p.: 82–85 |
| 1.070 | $CH_2CH_3$ | $CH_2CH_3$ | $SO_2CH_2CH=CH_2$ | |
| 1.071 | $C\equiv CH$ | $CH_2CH_3$ | $SO_2CH_3$ | |
| 1.072 | $C\equiv CH$ | $CH_2CH_3$ | $SO_2CH(CH_3)_2$ | |
| 1.073 | $C\equiv CH$ | $CH_2CH_3$ | $SO_2CH_2CH_2Cl$ | |
| 1.074 | $C\equiv CH$ | $CH_2CH_3$ | $SO_2CF_3$ | |
| 1.075 | $C\equiv CH$ | $CH_2CH_3$ | $SO_2CH=CH_2$ | |
| 1.076 | $C\equiv CH$ | $OCH_3$ | —H | m.p. 202–204 |
| 1.077 | $C\equiv CH$ | $OCH_3$ | $C(O)C(CH_3)_3$ | m.p. 204–206 |
| 1.078 | $C\equiv CSi(CH_3)_3$ | $OCH_3$ | $C(O)C(CH_3)_3$ | m.p. 169–171 |
| 1.079 | $C\equiv CSi(CH_3)_3$ | $OCH_3$ | —H | m.p. 173–174 |
| 1.080 | Br | $OCH_3$ | —H | m.p. 217–219 |
| 1.081 | Br | $OCH_3$ | $C(O)C(CH_3)_3$ | m.p. 173–175 |
| 1.082 | $CH_2CH_3$ | $CH_2CH_3$ | $C(O)C(CH_3)_2CH_2CH_3$ | m.p. 122–124° C. |
| 1.083 | $CH_2CH_3$ | $CH_2CH_3$ | $CON(CH_2CH_3)_2$ | m.p. 82–84 |
| 1.084 | $CH_2CH_3$ | $C(O)CH_3$ | $C(O)C(CH_3)_2CH_2CH_3$ | m.p. 138–139° C. |
| 1.085 | $CH_2CH_3$ | $C(O)CH_3$ | 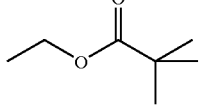 | |
| 1.086 | $CH_2CH_3$ | $C(O)CH_3$ | 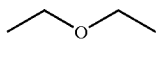 | |
| 1.087 | $CH_2CH_3$ | $C(O)CH_3$ |  | |
| 1.088 | $CH_2CH_3$ | $C(O)CH_3$ | 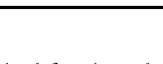 | |

The invention relates also to a method for the selective control of weeds in crops of useful plants, which method comprises treating the useful plants, their seeds or seedlings or the crop area thereof with a) a herbicidally effective amount of a herbicide of formula I, b) an amount, which is effective for antagonism of the herbicide, of a safener selected from cloquintocet, an alkali metal, alkaline earth metal, sulfonium or ammonium cation of cloquintocet, or cloquintocet-mexyl, mefenpyr, an alkali metal, alkaline earth metal, sulfonium or ammonium cation of mefenpyr, and mefenpyr-diethyl, and c) an additive comprising an oil of vegetable or animal origin or alkylated derivatives thereof, or a mineral oil or mixtures thereof.

Cultivated plants that may be protected against the harmful effect of the above-mentioned herbicides by means of the safeners cloquintocet, an alkali metal, alkaline earth metal, sulfonium or ammonium cation of cloquintocet, or cloquintocet-mexyl, mefenpyr, an alkali metal, alkaline earth metal, sulfonium or ammonium cation of mefenpyr, or mefenpyr-diethyl are especially cereals, cotton, soybeans, sugar beet, sugar cane, plantation crops, rape, maize and rice, more especially maize and cereals. Crops are to be understood as including those that have been made tolerant to herbicides or classes of herbicides by means of conventional breeding or genetic engineering methods, for example IMI Maize, Poast Protected Maize (sethoxydim tolerance), Liberty Link Maize, B.t./Liberty Link Maize, IMI/Liberty Link Maize, IMI/Liberty Link /B.t. Maize, Roundup Ready Maize and Roundup Ready/B.t. Maize.

The weeds to be controlled may be either dicotyledonous or, preferably, monocotyledonous weeds, for example the monocotyledonous weeds Avena, Agrostis, Phalaris, Lolium, Bromus, Alopecurus, Setaria, Digitaria, Brachiaria, Echinochloa, Panicum, Sorghum hal./bic., Rottboellia, Cyperus, Brachiaria, Echinochloa, Scirpus, Monochoria and Sagittaria and the dicotyledonous weeds Sinapis, Chenopodium, Stellaria, Galium, Viola, Veronica, Matricaria, Papaver, Solanum, Abutilon, Sida, Xanthium, Amaranthus, Ipomoea and Chrysanthemum.

Crop areas are areas of land on which the cultivated plants are already growing or in which the seeds of those cultivated plants have been sown, and also areas of land on which it is intended to grow those cultivated plants.

A safener in accordance with the invention may, depending on the intended purpose, be used to pre-treat the seed material of the cultivated plant (dressing the seed or the seedlings) or may be incorporated into the soil before or after sowing. It may, however, also be applied, alone or together with the herbicide and the oil additive, after the emergence of the plants. The treatment of the plants or seed with the safener can therefore, in principle, be effected independently of the time at which the herbicide is applied. The treatment of the plants can, however, also be carried out by applying the herbicide, oil additive and safener simultaneously (for example in the form of a tank mixture). The rate of application of the safener in relation to the herbicide depends largely on the method of application. In the case of field treatment, which is effected either using a tank mixture with a combination of the safener and the herbicide or by the separate application of the safener and the herbicide, the ratio of herbicide to safener is generally from 100:1 to 1:10, preferably from 20:1 to 1:1. In the case of field treatment, from 0.001 to 1.0 kg of safener/ha, preferably from 0.001 to 0.25 kg of safener/ha, are generally applied.

The rate of application of herbicide is generally from 0.001 to 2 kg/ha, but preferably from 0.005 to 1 kg/ha.

In the composition according to the invention, the amounts of oil additive employed are generally from 0.01 to 2%, based on the spray mixture. The oil additive can, for example, be added to the spray tank in the desired concentration after the spray mixture has been prepared.

Preferred oil additives comprise mineral oils or an oil of vegetable origin such as, for example, rapeseed oil, olive oil or sunflower oil, emulsified vegetable oil such as AMIGO® (obtainable from Rhône-Poulenc Canada Inc.), alkyl esters of oils of vegetable origin such as, for example, the methyl derivatives, or an oil of animal origin such as fish oil or beef tallow. Special preference is given to "Additive Type A", which contains as active components substantially 80% by weight alkyl esters of fish oils and 15% by weight methylated rapeseed oil, and also 5% by weight conventional emulsifiers and pH modifiers.

Especially preferred oil additives comprise alkyl esters of higher fatty acids ($C_8$–$C_{22}$), especially the methyl derivatives of $C_{12}$–$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Henkel subsidiary Cognis GMBH, Germany).

The application and action of the oil additives can be improved by combining them with surface-active substances such as non-ionic, anionic or cationic surfactants. Examples of suitable anionic, non-ionic and cationic surfactants are listed in WO 97/34485 on pages 7 and 8.

Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$–$C_{22}$ fatty alcohols having a degree of ethoxylation of from 5 to 40. Examples of commercially available preferred surfactants are the Genapol types (Clariant AG, Muttenz, Switzerland). The concentration of the surface-active substances based on the total additive is generally from 1 to 30% by weight.

Examples of oil additives consisting of mixtures of oils or mineral oils or derivatives thereof with surfactants are Edenor ME SU®, Turbocharge® (Zeneca Agro, Stoney Creek, Ontario, Canada) or, more especially, Actipron® (BP Oil UK Limited, GB). The addition of an organic solvent to the oil additive/surfactant mixture can, furthermore, bring about a further increase in action. Suitable solvents are, for example Solvesso® (ESSO) or Aromatic Solvent® (Exxon Corporation) types. The concentration of those solvents can be from 10 to 80%, by weight, of the total weight.

Such oil additives, which are also described, for example, in U.S. Pat. No. 4,834,908, are especially preferred for the composition according to the invention. An especially preferred oil additive is known under the name MERGE®, can be obtained from the BASF Corporation and is basically described, for example, in U.S. Pat. No. 4,834,908 in col. 5, as Example COC-1. A further oil additive that is preferred according to the invention is SCORE® (Novartis Crop Protection Canada.)

The compositions according to the invention are suitable for all methods of application that are customary in agriculture, for example pre-emergence application, post-emergence application and seed dressing.

In the case of seed dressing, from 0.001 to 10 g of safener/kg of seed, preferably from 0.05 to 6 g of safener/kg of seed, are generally applied. When the safener is applied in liquid form shortly before sowing, with swelling of the seed, it is advantageous to use safener solutions that comprise the active ingredient in a concentration of from 1 to 10 000 ppm, preferably from 10 to 1000 ppm.

For application, the safeners according to the invention or combinations of those safeners with the herbicides of formula I and the oil additives are advantageously processed, together with the adjuvants conventionally employed in formulation technology, into formulations, for example into emulsifiable concentrates, coatable pastes, directly sprayable or dilutable solutions, dilute emulsions, wettable powders, soluble powders, dusts, granules or microcapsules.

Such formulations are described, for example, in WO 97/34485, on pages 9 to 13. The formulations are prepared in known manner, for example by intimately mixing and/or grinding the active ingredients with liquid or solid formulation adjuvants, for example solvents or solid carriers. Furthermore, surface-active compounds (surfactants) may additionally be used in the preparation of the formulations. Solvents and solid carriers that are suitable for that purpose are mentioned, for example, in WO 97/34485 on page 6.

Suitable surface-active compounds are, depending on the nature of the active ingredient of formula I being formulated, non-ionic, cationic and/or anionic surfactants and mixtures of surfactants having good emulsifying, dispersing and wetting properties. Examples of suitable anionic, non-ionic and cationic surfactants are listed, for example, in WO 97/34485 on pages 7 and 8. Furthermore, the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, MunichNienna, 1981 and M. and J. Ash, "Encyclopedia of Surfactants", Vol I–III, Chemical Publishing Co., New York, 1980–81, are also suitable for preparation of the herbicidal compositions according to the invention.

The herbicidal formulations generally comprise from 0.1 to 99% by weight, especially from 0.1 to 95% by weight, of active ingredient mixture comprising the compound of formula I together with the safeners according to the invention, from 0.01 to 2% by weight of the oil additive according to the invention, from 1 to 99.9% by weight of a solid or liquid formulation adjuvant and from 0 to 25% by weight, especially from 0.1 to 25% by weight, of a surfactant. Whereas commercial products will preferably be formulated as concentrates, the end user will normally employ dilute formulations.

The compositions may also comprise further additives such as stabilisers, for example vegetable oils or epoxidised vegetable oils (epoxidised coconut oil, rapeseed oil or soybean oil), antifoams, for example silicone oil, preservatives, viscosity regulators, binders and tackifiers, as well as fertilisers or other active ingredients. There are various suitable methods and techniques for using safeners according to the invention or compositions comprising them for protecting cultivated plants against harmful effects of herbicides of formula I; the following are examples:

i) Seed Dressing a) Dressing the seeds with a wettable powder formulation of an active ingredient from the safeners according to the invention by shaking in a vessel until the formulation is uniformly distributed over the seed surface (dry dressing). Approximately from 1 to 500 g of active ingredient of the safeners according to the invention (from 4 g to 2 kg of wettable powder) are used per 100 kg of seed.

b) Dressing the seeds with an emulsifiable concentrate of the safeners according to the invention according to method a) (wet dressing).

c) Dressing by immersing the seed in a liquid formulation comprising from 100 to 1000 ppm of safeners according to the invention for from 1 to 72 hours and, if desired, subsequently drying the seeds (immersion dressing).

Dressing the seed or treating the germinated seedlings are naturally the preferred methods of application because the treatment with the active ingredient is directed wholly at the target crop. Generally from 1 to 1000 g of antidote, preferably from 5 to 250 g of antidote, are used per 100 kg of seed, although, depending on the method employed, which also allows the addition of other active ingredients or micronutrients, amounts that exceed or fall short of the specified concentration limits may be employed (repeat dressing).

ii) Application in the Form of a Tank Mixture

A liquid formulation of a mixture of antidote and herbicide (ratio of the one to the other from 20:1 to 1:100) is used, the rate of application of herbicide being from 0.005 to 5.0 kg per hectare. The oil additive can be added to the tank mixture in an amount of, preferably, from 0.01 to 2% by weight. Such tank mixtures are applied before or after sowing.

iii) Application to the Seed Furrow

The safener is introduced into the open, sown seed furrow in the form of an emulsifiable concentrate, a wettable powder or granules. After the seed furrow has been covered, the herbicide, optionally in combination with the oil additive, is applied pre-emergence in the normal manner.

iv) Controlled Release of the Active Ingredient

The safener is applied in solution to granulated mineral carriers or polymerised granules (urea-formaldehyde) and dried. If desired, a coating may be applied (coated granules) which enables the active ingredient to be released in metered amounts over a predetermined period of time.

Preferred formulations have especially the following compositions (%=percent by weight; 'active ingredient mixture' denotes the mixture of the compound of formula I with the safeners according to the invention and, optionally, the oil additives)

| Emulsifiable concentrates: | |
|---|---|
| active ingredient mixture: | from 1 to 90%, preferably from 5 to 20% |
| surface-active agent: | from 1 to 30%, preferably from 10 to 20% |
| liquid carrier: | from 5 to 94%, preferably from 70 to 85% |
| Dusts: | |
| active ingredient mixture: | from 0.1 to 10%, preferably from 0.1 to 5% |
| solid carrier: | from 99.9 to 90%, preferably from 99.9 to 99% |
| Suspension concentrates: | |
| active ingredient mixture: | from 5 to 75%, preferably from 10 to 50% |
| water: | from 94 to 24%, preferably from 88 to 30% |
| surface-active agent: | from 1 to 40%, preferably from 2 to 30% |
| Wettable powders: | |
| active ingredient mixture: | from 0.5 to 90%, preferably from 1 to 80% |
| surface-active agent: | from 0.5 to 20%, preferably from 1 to 15% |
| solid carrier: | from 5 to 95%, preferably from 15 to 90% |
| Granules: | |
| active ingredient mixture: | from 0.1 to 30%, preferably from 0.1 to 15% |
| solid carrier: | from 99.5 to 70%, preferably from 97 to 85% |

The Examples that follow illustrate the invention further. They do not limit the invention.

Formulation Examples for Mixtures of Herbicides of Formula I, Safener and oil Additive (%=Percent by Weight)

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyethylene glycol ether (36 mol of ethylene oxide) | 4% | — | 4% | 4% |
| octylphenoxypolyethylene glycol ether (7–8 mol of ethylene oxide) | — | 4% | — | 2% |
| cyclohexanone | — | — | 10% | 20% |
| aromatic $C_9$–$C_{12}$ hydrocarbon mixture | 85% | 78% | 55% | 16% |

Emulsions of any desired concentration can be prepared from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy- | — | 20% | 20% | — |

-continued

| F2. Solutions | a) | b) | c) | d) |
|---|---|---|---|---|
| propoxy)-propane | | | | |
| polyethylene glycol (mol. wt. 400) | 20% | 10% | — | — |
| N-methyl-2-pyrrolidone | — | — | 30% | 10% |
| aromatic $C_9$–$C_{12}$ hydrocarbon mixture | 75% | 60% | — | — |

The solutions are suitable for application in the form of micro-drops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenoxypolyethylene glycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier material (Æ 0.1–1 mm) for example $CaCO_3$ or $SiO_2$ | 99.0% | 93% | 83% |

The active ingredient is dissolved in methylene chloride, the solution is sprayed onto the carrier, and the solvent is subsequently evaporated off in vacuo.

| F5. Coated granules | a) | b) | c) |
|---|---|---|---|
| active ingredient mixture | 0.1% | 5% | 15% |
| polyethylene glycol (mol. wt. 200) | 1.0% | 2% | 3% |
| highly dispersed silicic acid | 0.9% | 1% | 2% |
| inorganic carrier material (Æ 0.1–1 mm) for example $CaCO_3$ or $SiO_2$ | 98.0% | 92% | 80% |

The finely ground active ingredient is uniformly applied, in a mixer, to the carrier material moistened with polyethylene glycol, yielding non-dusty coated granules.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed with the adjuvants, and the mixture is ground, moistened with water, extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenoxypolyethylene glycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical to formulate the active ingredient of formula I (optionally in combination with the oil additive) and the safener separately and then, shortly before application, to bring them together in the applicator in the desired mixing ratio in the form of a "tank mixture" in water. The active ingredient of formula I and the safener can also be formulated separately and, shortly before application, brought together in the applicator in the desired mixing ratio in the form of a "tank mixture" in water, with the oil additive being added thereafter.

The herbicidally selective action of the compositions according to the invention is illustrated in the following Examples.

Biological Examples

Example B1

Post-emergence Test:

The test plants are grown in pots under greenhouse conditions until the post-application stage. A standard soil is used as cultivation substrate. At a post-emergence stage, the herbicides, both on their own and in admixture with safeners and/or oil additives, are applied to the test plants or to cultivated plants seed-dressed with safeners. The application is carried out using an emulsion (prepared from an emulsifiable concentrate (Example F1, c)) of the test substances. The rates of application depend on the optimum doses ascertained under field conditions and greenhouse conditions. The tests are evaluated after from 2 to 4 weeks (100% action=complete destruction, 0% action=no phytotoxic action).

The rate of application of herbicide is in each case 25 g/ha; the rate of application of cloquintocet-mexyl is 6.25 g/ha. As oil additive, MERGE® is used in a concentration of 1% by weight of the spray mixture.

TABLE B1.1

Herbicidal action of compound no. 1.007 and compound no. 1.008:

| Test plant | compound no. 1.007 | compound no. 1.008 |
|---|---|---|
| wheat | 0 | 0 |
| Apera | 60 | 25 |
| Alopecurus | 10 | 20 |
| Avena | 10 | 20 |

In this test, herbicide no. 1.007 and herbicide no. 1.008, at a rate of application of 25 g/ha, exhibit only slight to moderate herbicidal action on the weeds. The cultivated plant (wheat) is not damaged at that rate of application.

TABLE B1.2

Herbicidal action of compound no. 1.007 and compound no. 1.008 in combination with the safener cloquintocet-mexyl:

| Test plant | compound no. 1.007 + cloquintocet-mexyl | compound no. 1.008 + cloquintocet-mexyl |
|---|---|---|
| wheat | 0 | 0 |
| Apera | 45 | 25 |
| Alopecurus | 20 | 15 |
| Avena | 20 | 15 |

In this test, the addition of 6.25 g/ha of cloquintocet-mexyl results in a reduction in the herbicidal action of compound no. 1.008 in the case of all the weeds tested, whereas in the case of compound no. 1.007 the herbicidal action on Apera is reduced from 60% to just 45% and the herbicidal action on Alopecurus and Avena is increased from 10% to a still completely unsatisfactory 20%. The cultivated plant (wheat) is not damaged in the case of this mixture.

TABLE B1.3

Herbicidal action of compound no. 1.007 and compound no. 1.008, in combination with MERGE ®:

| Test plant | compound no. 1.007 + MERGE ®: | compound no. 1.008 + MERGE ®: |
|---|---|---|
| wheat | 60 | 50 |
| Apera | 85 | 90 |
| Alopecurus | 90 | 85 |
| Avena | 95 | 95 |

In this test, compound no. 1.007 and compound no. 1.008, in combination with MERGE®, exhibit strong herbicidal action on all weeds tested. At the same time, however, major damage to the wheat is observed.

TABLE B1.4

Herbicidal action of compound no. 1.007 and compound no. 1.008, in combination with cloquintocet-mexyl and MERGE ®:

| Test plant | compound no. 1.007 + cloquintocet-mexyl + MERGE | compound no. 1.008 + cloquintocet-mexyl + MERGE |
|---|---|---|
| wheat | 0 | 0 |
| Apera | 85 | 90 |
| Alopecurus | 90 | 90 |
| Avena | 95 | 90 |

The combination of each of the herbicides with cloquintocet-mexyl and MERGE® surprisingly results in outstanding selectivity of the mixture with respect to the cultivated plant. Whereas the weeds are almost completely destroyed, the wheat is to a very large extent protected from the phytotoxic action of the herbicides.

Example B2

Post-emergence Test (Description of Test as for Example B1):

In this test, the herbicidal action of compound no. 1.008 in combination with cloquintocet-mexyl is compared to the action of compound no. 1.008 in combination with cloquintocet-mexyl and various oil additives according to the invention. The rate of application of herbicide is 8 g/ha in each case; the rate of application of cloquintocet-mexyl is 2 g/ha. The oil additive is used in a concentration of 0.7% by weight of the spray mixture. The results are given in the following Tables.

TABLE B2.1

Herbicidal action of compound no. 1.008 in combination with cloquintocet-mexyl and of compound no. 1.008 in combination with cloquintocet-mexyl and Emery ® 2231:

| Test plant | compound no. 1.008 + cloquintocet-mexyl | compound no. 1.008 + cloquintocet-mexyl + Emery ® 2231 |
|---|---|---|
| wheat | 10 | 0 |
| Alopecurus | 0 | 60 |
| Lolium | 0 | 80 |

The combination of compound no. 1.008 with cloquintocet-mexyl at the rate of application tested shows no herbicidal action against the weeds but does show phytotoxic action of 10% in the case of wheat. When that mixture is combined with the oil additive Emery® 2231, however, the weeds are severely damaged. Surprisingly, the useful plant is completely protected from the phytotoxic action of the herbicide (0% damage). Further Examples of the surprising increase in selectivity of the compositions according to the invention are given in Tables B2.2 and B2.3 which follow.

TABLE B2.2

Herbicidal action of compound no. 1.008
in combination with cloquintocet-mexyl
and of compound no. 1.008 in combination
with cloquintocet-mexyl and AMIGO ®:

| Test plant | compound no. 1.008 + cloquintocet-mexyl | compound no. 1.008 + cloquintocet-mexyl + AMIGO ® |
|---|---|---|
| wheat | 10 | 0 |
| Alopecurus | 0 | 50 |
| Lolium | 0 | 90 |

TABLE B2.3

Herbicidal action of compound no. 1.008
in combination with cloquintocet-mexyl
and of compound no. 1.008 in combination
with cloquintocet-mexyl and Additive Type A:

| Test plant | compound no. 1.008 + cloquintocet-mexyl | compound no. 1.008 + cloquintocet-mexyl + Additive Type A |
|---|---|---|
| wheat | 10 | 0 |
| Alopecurus | 0 | 30 |
| Lolium | 0 | 60 |

What is claimed is:

1. A selectively herbicidal composition which, in addition to comprising customary inert formulation adjuvants, comprises as active ingredient a mixture of
   a) a herbicidally effective amount of a compound of formula I

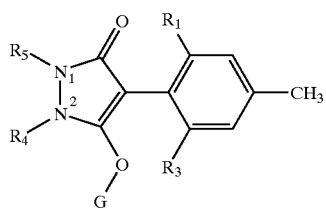

(I)

wherein $R_1$ and $R_3$ are, each independently of the other, halogen, nitro, cyano, $C_1$–$C_4$alkyl, $C_2$–$C_4$alkenyl, $C_2$–$C_4$alkynyl, $C_1$–$C_4$haloalkyl, $C_2$–$C_6$haloalkenyl, $C_3$–$C_6$cycloalkyl, halo-substituted $C_3$–$C_6$cycloalkyl, $C_2$–$C_6$alkoxyalkyl, $C_2$–$C_6$alkylthioalkyl, hydroxy, mercapto, $C_1$–$C_6$alkoxy, $C_3$–$C_6$alkenyloxy, $C_3$–$C_6$alkynyloxy, carbonyl, carboxyl, $C_1$–$C_4$alkylcarbonyl, $C_1$–$C_4$hydroxyalkyl, $C_1$–$C_4$alkoxycarbonyl, $C_1$–$C_4$alkylthio, $C_1$–$C_4$alkylsulfinyl, $C_1$–$C_4$alkylsulfonyl, amino, $C_1$–$C_4$alkylamino or di($C_1$–$C_4$alkyl)amino;

$R_4$ and $R_5$ together are a group
—C—$R_6$($R_7$)—O—C—$R_8$($R_9$)—C—$R_{10}$($R_{11}$)—C—$R_{12}$($R_{13}$)— ($Z_1$),
—C—$R_{14}$($R_{15}$)—C—$R_{16}$($R_{17}$)—O—C—$R_{18}$($R_{19}$)—C—$R_{20}$($R_{21}$)— ($Z_2$), or
—C—$R_{22}$($R_{23}$)—C—$R_{24}$($R_{25}$)—C—$R_{26}$($R_{27}$)—O—C—$R_{28}$($R_{29}$)— ($Z_3$), wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are, each independently of the others, hydrogen, halogen, $C_1$–$C_4$alkyl or $C_1$–$C_4$haloalkyl, it being possible for an alkylene ring, which together with the carbon atoms of the groups $Z_1$, $Z_2$ or $Z_3$ contains from 2 to 6 carbon atoms and which may be interrupted by oxygen, to be either fused or spiro-bound to the carbon atoms of the groups $Z_1$, $Z_2$ or $Z_3$ or that alkylene ring bridges at least one ring atom of the groups $Z_1$, $Z_2$ or $Z_3$;

G is hydrogen, —C($X_1$)—$R_{30}$, —C($X_2$)—$X_3$—$R_{31}$, —C($X_4$)—N($R_{32}$)—$R_{33}$, —SO$_2$—$R_{34}$, an alkali metal, alkaline earth metal, sulfonium or ammonium cation, or —P($X_5$)($R_{35}$)—$R_{36}$ or —CH$_2$—$X_6$—$R_{37}$;

$X_1$, $X_2$, $X_3$, $X_4$, $X_5$ and $X_6$ are, each independently of the others, oxygen or sulfur;

$R_{30}$, $R_{31}$, $R_{32}$ and $R_{33}$ are, each independently of the others, hydrogen, $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_{10}$alkoxy-alkyl, $C_4$–$C_{10}$alkenyloxy-alkyl, $C_4$–$C_{10}$alkynyloxy-alkyl, $C_2$–$C_{10}$alkylthio-alkyl, $C_1$–$C_5$alkysulfoxyl-$C_1$–$C_5$alkyl, $C_1$–$C_5$alkylsulfonyl-$C_1$–$C_5$alkyl, $C_2$–$C_8$alkylideneamino-oxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$aminocarbonyl-$C_1$–$C_5$alkyl, $C_2$–$C_8$dialkylamino-carbonyl-$C_1$–$C_5$alkyl, $C_1$–$C_5$alkylcarbonylamino-$C_1$–$C_5$alkyl, $C_2$–$C_5$alkylcarbonyl-($C_1$–$C_5$alkyl)-aminoalkyl, $C_3$–$C_6$trialkylsilyl-$C_1$–$C_5$alkyl, phenyl-$C_1$–$C_5$alkyl, heteroaryl-$C_1$–$C_5$alkyl, phenoxy-$C_1$–$C_5$alkyl, heteroaryloxy-$C_1$–$C_5$alkyl, $C_2$–$C_5$alkenyl, $C_2$–$C_5$haloalkenyl, $C_3$–$C_8$cycloalkyl, phenyl, or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenyl or heteroaryl or heteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted heteroarylamino, diheteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diheteroarylamino, phenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenylamino, diphenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diphenylamino, $C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$Cycloalkylamino, di-$C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted di-$C_3$–$C_7$cycloalkylamino, $C_3$–$C_7$cycloalkoxy or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkoxy;

$R_{34}$, $R_{35}$ and $R_{36}$ are hydrogen, $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_{10}$alkoxy-alkyl, $C_4$–$C_{10}$alkenyloxy-alkyl, $C_4$–$C_{10}$alkynyloxy-alkyl, $C_2$–$C_{10}$alkylthio-alkyl, $C_1$–$C_5$alkysulfoxyl-$C_1$–$C_5$alkyl, $C_1$–$C_5$alkylsulfonyl-$C_1$–$C_5$alkyl, $C_2$–$C_8$alkylideneamino-oxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$aminocarbonyl-$C_1$–$C_5$alkyl, $C_2$–$C_8$dialkylamino-carbonyl-$C_1$–$C_5$alkyl, $C_1$–$C_5$alkylcarbonylamino-$C_1$–$C_5$alkyl, $C_2$–$C_5$alkylcarbonyl-($C_1$–$C_5$alkyl)-aminoalkyl, $C_3$–$C_6$trialkylsilyl-$C_1$–$C_5$alkyl, phenyl-$C_1$–$C_5$alkyl, heteroaryl-$C_1$–$C_5$alkyl, phenoxy-$C_1$–$C_5$alkyl, heteroaryloxy-$C_1$–$C_5$alkyl, $C_2$–$C_5$alkenyl, $C_2$–$C_5$haloalkenyl, $C_3$–$C_8$cycloalkyl, phenyl, or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenyl or heteroaryl or heteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted heteroarylamino, diheteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diheteroarylamino, phenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenylamino, diphenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diphenylamino, $C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkylamino, di-$C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted di-$C_3$–$C_7$cycloalkylamino, $C_3$–$C_7$cycloalkoxy, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkoxy, $C_1$–$C_{10}$alkoxy, $C_1$–$C_{10}$haloalkoxy, $C_1$–$C_5$alkylamino, $C_2$–$C_8$dialkylamino and benzyloxy or phenoxy, it being possible for the benzyl and phenyl groups themselves to be substituted by $C_1$–$C_3$alkyl, $C_1$–$C_3$haloalkyl, $C_1$–$C_3$alkoxy, $C_1$–$C_3$haloalkoxy, halogen, cyano, formyl, acetyl, propionyl, carboxyl, $C_1$–$C_5$alkoxycarbonyl, methylthio, ethylthio or by nitro; and $R_{37}$ is $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, $C_2$–$C_8$dialkylamino-$C_1$–$C_5$alkyl, $C_3$–$C_7$cycloalkyl-$C_1$–$C_5$alkyl, $C_2$–$C_{10}$alkoxy-alkyl, $C_4$–$C_{10}$alkenyloxy-alkyl, $C_4$–$C_{10}$alkynyloxy-alkyl, $C_2$–$C_{10}$alkylthio-alkyl, $C_1$–$C_5$alkysulfoxyl-$C_1$–$C_5$alkyl, $C_1$–$C_5$alkylsulfonyl-$C_1$–$C_5$alkyl, $C_2$–$C_8$alkylideneamino-oxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$aminocarbonyl-$C_1$–$C_5$alkyl, $C_2$–$C_8$dialkylamino-carbonyl-$C_1$–$C_5$alkyl, $C_1$–$C_5$alkylcarbonylamino-$C_1$–$C_5$alkyl, $C_2$–$C_5$alkylcarbonyl-($C_1$–$C_5$alkyl)-aminoalkyl, $C_3$–$C_6$trialkylsilyl-$C_1$–$C_5$alkyl, phenyl-$C_1$–$C_5$alkyl, heteroaryl-$C_1$–$C_5$alkyl, phenoxy-$C_1$–$C_5$alkyl, heteroaryloxy-$C_1$–$C_5$alkyl, $C_2$–$C_5$alkenyl, $C_2$–$C_5$haloalkenyl, $C_3$–$C_8$cycloalkyl, phenyl, or $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenyl or heteroaryl, or heteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted heteroarylamino, diheteroarylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diheteroarylamino, phenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted phenylamino, diphenylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted diphenylamino, $C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkylamino, di-$C_3$–$C_7$cycloalkylamino, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted di-$C_3$–$C_7$Cycloalkylamino, $C_3$–$C_7$cycloalkoxy, $C_1$–$C_3$alkyl-, $C_1$–$C_3$haloalkyl-, $C_1$–$C_3$alkoxy-, $C_1$–$C_3$haloalkoxy-, halo-, cyano- or nitro-substituted $C_3$–$C_7$cycloalkoxy or $C_1$–$C_{10}$alkylcarbonyl; and salts and diastereoisomers of the compounds of formula I, with the proviso that $R_1$ and $R_3$ are not simultaneously methyl;

b) an amount, which is effective for antagonism of the herbicide, of a safener selected from cloquintocet, an alkali metal, alkaline earth metal, sulfonium or ammonium cation of cloquintocet, or cloquintocet-mexyl, mefenpyr, an alkali metal, alkaline earth metal, sulfonium or ammoniurh cation of mefenpyr, and mefenpyr-diethyl; and c) an additive comprising an oil of vegetable or animal origin, or a mineral oil, alkyl esters thereof or mixtures of those oils.

2. A method of selectively controlling weeds and grasses in crops of useful plants, which comprises treating the useful plants, their seeds or seedlings or the crop area thereof with a composition according to claim 1.

3. A method according to claim 2, wherein the crops of useful plants are cereals or maize.

* * * * *